(12) United States Patent
Guhaniyogi

(10) Patent No.: US 11,219,768 B2
(45) Date of Patent: Jan. 11, 2022

(54) AV SYNCHRONY WITH A VENTRICULAR LEADLESS PACEMAKER USING VARYING VENTRICULAR MEASURES

(71) Applicant: BIOTRONIK SE & CO. KG, Berlin (DE)

(72) Inventor: Shayan Guhaniyogi, Portland, OR (US)

(73) Assignee: BIOTRONIK SE & Co. KG, Berlin (DE)

(*) Notice: Subject to any disclaimer, the term of this patent is extended or adjusted under 35 U.S.C. 154(b) by 111 days.

(21) Appl. No.: 16/825,659

(22) Filed: Mar. 20, 2020

(65) Prior Publication Data

US 2020/0306545 A1     Oct. 1, 2020

Related U.S. Application Data

(60) Provisional application No. 62/827,208, filed on Apr. 1, 2019.

(51) Int. Cl.
    *A61N 1/37*       (2006.01)
    *A61N 1/375*      (2006.01)
    *A61N 1/365*      (2006.01)

(52) U.S. Cl.
CPC ........ *A61N 1/3702* (2013.01); *A61N 1/36542* (2013.01); *A61N 1/36564* (2013.01); *A61N 1/36578* (2013.01); *A61N 1/3706* (2013.01); *A61N 1/3756* (2013.01); *A61N 1/37512* (2017.08)

(58) Field of Classification Search
None
See application file for complete search history.

(56) References Cited

U.S. PATENT DOCUMENTS 9,399,140 B2    7/2016   Cho et al.
2017/0239472 A1*   8/2017   Zhang ................ A61N 1/37264

FOREIGN PATENT DOCUMENTS

EP        3444008 A1    2/2019

\* cited by examiner

*Primary Examiner* — Brian T Gedeon
(74) *Attorney, Agent, or Firm* — Laurence A. Greenberg; Werner H. Stemer; Ralph E. Locher

(57) ABSTRACT

An implantable pacemaker is configured to provide electrical pacing pulses to the heart of a patient. The pacemaker has a pulse generator configured to generate the electrical pacing pulses, at least one pacing electrode to apply the electrical pacing pulses to the heart, a sensing unit configured to sense events of electrical activity of a ventricle of the heart, a sensor configured to measure a signal relating to the patient, and a memory configured to store values of a parameter. The pacemaker is configured to be operated in a first mode to generate a reference curve and to select a target range of values of the parameter corresponding to a desired range of atrioventricular delays. The pacemaker is further configured to be operated in a second mode for approaching the target range.

15 Claims, 4 Drawing Sheets

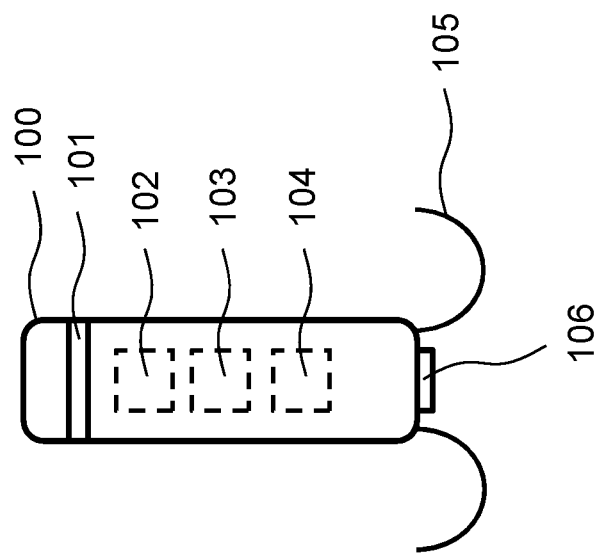

AV SYNCHRONY WITH A VENTRICULAR LEADLESS PACEMAKER USING VARYING VENTRICULAR MEASURES

CROSS-REFERENCE TO RELATED APPLICATION

This application claims the benefit, under 35 U.S.C. § 119(e), of provisional patent application No. 62/827,208, filed Apr. 1, 2019; the prior application is herewith incorporated by reference in its entirety.

BACKGROUND OF THE INVENTION

Field of the Invention

The present invention relates to an implantable pacemaker as well as to a method for operating an implantable pacemaker.

Concerning cardiac pacing, maintaining atrioventricular (AV) synchrony is of high importance. AV synchrony means that in the (normal) activation sequence of the heart the atria contract first and then, after an appropriate delay, which is denoted as atrioventricular (AV) delay, the ventricles contract. When the timing between the two chambers goes out of synchronization, less blood is delivered on each beat and the cardiovascular output decreases.

Cardiac pacemakers operating in VVI mode (i.e. ventricular pacing and sensing) often create AV dyssynchrony, resulting in suboptimal cardiovascular output. By tracking the atrial activity and pacing the ventricle only after detecting an atrial contraction (e.g. VDD mode) AV synchrony can be re-established. In traditional pacemakers VDD is achieved by placing a sensing electrode in the atrial chamber by way of a lead. However this is, by definition, not possible with implantable leadless pacemakers (ILP). A leadless pacemaker placed in the ventricle must therefore be able to provide AV synchrony without a lead in the atrial chamber. Existing solutions e.g. attempt direct measures of atrial contraction from within the ventricle using electrical, impedance, motion, or other signal sources; however this can be challenging because the atrial component of these signals are often very small, inconsistent, or non-existent.

The drawback of solutions attempting a direct measure of atrial contraction from the ventricle is that the atrial component of many signal sources when measured in the ventricle is small, inconsistent, or non-existent, making atrial tracking challenging. Furthermore, the drawbacks of solutions employing an atrial sensing extension are that they introduce an additional component to the device, which is not desirable.

U.S. patent publication No. 2017/0239472 A1 discloses a medical device system for predicting a patient response to a cardiac therapy. The system includes electrodes for delivering cardiac pacing pulses to a patient's heart coupled to a cardiac sensing module and a cardiac pacing module for generating cardiac pacing pulses and controlling delivery of the pacing pulses at multiple pace parameter settings. A processor is enabled to receive heart sound signals from an acoustical sensor, derive a plurality of heart sound signal parameters from the heart sound signals, and determine a trend of each of the plurality of heart sound signal parameters with respect to the plurality of pace parameter settings. Further, an external display is configured to present the trend of at least one heart sound parameter with respect to the plurality of pace parameter settings.

SUMMARY OF THE INVENTION

Based on the above, it is an objective of the present invention to provide AV synchrony for a pacemaker, particularly for an implantable intracardiac (e.g. leadless) pacemaker that does not rely on small, inconsistent, or non-existent atrial components of signals, and does not rely on an additional sensing extension.

This objective is solved by an implantable pacemaker having the features of the independent claim. Further embodiments are stated in the corresponding sub claims and are described below.

An implantable pacemaker is disclosed which is configured to provide electrical pacing pulses to the heart of a patient when the pacemaker is implanted in the patient (particularly in ventricle of the patient). The pacemaker comprises:

a) a pulse generator configured to generate electrical pacing pulses, b) at least one pacing electrode to apply the electrical pacing pulses to the heart, c) a sensing unit configured to sense events of electrical activity of a ventricle of the heart, wherein the respective event corresponds to a contraction of the ventricle, d) a sensor configured to measure a physiological signal generated by the patient, and e) a memory configured to store values of a parameter.

The pacemaker is configured to be operated in a first mode for a pre-defined time period and thereafter and in a second mode. In the first mode, the pacemaker is configured to apply electrical pacing pulses generated by the pulse generator to the ventricle via the at least one pacing electrode unless the sensing unit senses an event, and to determine from the signal for each applied electrical pacing pulse or sensed event a value of a parameter that depends on the atrioventricular (AV) delay of the heart. The pacemaker is configured to store the values of the parameter in the memory, and the pacemaker is further configured to generate in the first mode a reference curve which associates each determined value of the parameter with an atrioventricular delay value, and to select a target range of values of the parameter corresponding to a desired range of atrioventricular delays. The pacemaker is further configured to be operated in a second mode, wherein in the second mode, the pacemaker is configured to determine a value of the parameter for every heartbeat of the patient, When the respective value of the parameter determined in the second mode for a heartbeat is outside the target range, the pacemaker is configured to adjust the timing of an electrical pacing pulse for the next heartbeat such that a determined value of the parameter for a succeeding heartbeat approaches the target range as a way to provide AV synchrony. It is sufficient for the parameter to approach the target range over several beats (e.g. 5 to 20 beats) so that it finally lies within the target range. It does not necessarily have to lie within the target range for the very next beat.

Preferably, the pacemaker is an intracardiac pacemaker, wherein particularly the intracardiac pacemaker is configured to be implanted into a ventricle of the heart of the patient. Particularly, the intracardiac pacemaker is an implantable leadless pacemaker, i.e. comprises a pacing electrode arranged on a housing of the pacemaker, wherein the housing is configured to be anchored to the heart wall in the ventricle or comprises a fixation element for fixation of the pacemaker to cardiac tissue. However, alternatively, the pacemaker can also comprise a flexible lead extending from a housing of the pacemaker, wherein the sensor (e.g. pressure sensor, accelerometer, microphone, electrodes) to measure the signal from which the parameter is derived can be arranged in the lead, particularly in a tip of the lead.

Further, according to an embodiment of the pacemaker the signal is indicative of one of: a ventricular pressure (wherein particularly the sensor is a pressure sensor), a heart sound (wherein particularly the sensor is a microphone or an accelerometer), a cardiac-wall motion (wherein particularly the sensor is an accelerometer), a ventricular impedance (wherein particularly the sensor comprises electrodes for measuring said impedance). Particularly, the heart sound can be the S1 heart sound of the patient.

Further, wherein for generating the reference curve, the pacemaker is configured to sort the values of the parameter determined in the first mode according to an assumed curve type. I.e. in case the curve type is monotonically decreasing, the determined values are ordered such that they decrease. Particularly, due to the fact that the pacemaker is in WI mode (i.e. in the first mode), the values stored are a mix of those resulting from intrinsic synchronized contractions, and paced asynchronous contractions. Consequently, the stored values of the parameter correspond to a range of AV delays. Although the actual AV delay for each value of the parameter is not measured, because the parameter is known to monotonically decrease with longer AV delays, the values of the parameter can be sorted to generate a reference curve. The smallest values of the parameter on this curve corresponds to AV delays which were too long, while the largest values of the parameter on the reference curve correspond to AV delays which were too short.

Furthermore, in an alternative embodiment, also a parameter can be used that is related to a monotonically increasing, a bell-shaped, or a parabolic curve type.

According to a preferred embodiment, wherein the parameter is the amplitude of the S1 heart sound of the patient. The S1 heart sound is a result of ventricular contraction pushing blood against the closing tricuspid/mitral valves. Particularly, according to the literature the amplitude of S1 monotonically decreases with longer AV delays.

Thus, particularly when the parameter is the S1 amplitude, the target range corresponds to an interval between the largest and the smallest determined value of the parameter (e.g. amplitude of the S1 heart sound).

Particularly, in an embodiment, when the respective value of the parameter (e.g. amplitude of the S1 heart sound) is below the target range, the pacemaker is configured to adjust the timing of the next electrical pacing pulse to an earlier timing so as to generate a value of the parameter for a succeeding heartbeat within the target range in order to provide AV synchrony, and wherein when the respective value of the parameter (amplitude of the S1 heart sound) is above the target range, the pacemaker is configured to adjust the timing of the next electrical pacing pulse to a later timing so as to generate a value of the parameter for a succeeding heartbeat within the target range in order to provide AV synchrony.

According to another embodiment of the pacemaker the curve type of the reference curve is bell-shaped. According to the literature, the stroke volume has a bell-shaped relationship to AV delay, and therefore a stroke volume parameter measured via the ventricular impedance signal and/or the cardiac-wall motion signal would be represented by a bell-shaped curve in this embodiment. Here, particularly, the target range is an interval that comprises the largest determined value of the parameter (i.e. near the peak of the reference curve).

According to an embodiment, particularly in case of a bell-shaped reference curve, when the respective value of the parameter is below the target range, the pacemaker is configured to adjust the timing of the next electrical pacing pulse to an earlier timing, wherein in case the value of the parameter increases on the next heartbeat, the pacemaker is configured to continue to shorten the timing of the electrical pacing pulse for each succeeding heartbeat until the value of the parameter reaches the target range. In case the value of the parameter decreases, the pacemaker is configured to lengthen the timing of the electrical pacing pulse for each succeeding heartbeat until the value of the parameter reaches the target range.

In another embodiment of the pacemaker or method, the algorithm could use other parameters besides amplitude for the specific signal being measured. The other metrics could include width, frequency, spread, or variation of the signal. The pacemaker can comprise the appropriate processing components to calculate such metrics. For example, the pacemaker can be configured to generate a curve of S1 heart sound frequency vs AV delay instead of S1 amplitude vs AV delay.

In another embodiment, the pacemaker or method can use multiple ventricular parameters with different relationships to AV delays (e.g. one with a monotonically increasing relationship, and another with a parabolic relationship) at the same time to maintain an optimal range of AV delays.

In another embodiment, the pacemaker or method can be extended to a single-chamber pacemaker that has the necessary sensors (pressure, accelerometer, microphone, electrodes) to measure the ventricular contraction parameters in the tip of a lead attached to the pacemaker.

Furthermore, according to yet another aspect, a method for operating an implantable pacemaker (particularly an implantable leadless pacemaker or intracardiac pacemaker) is disclosed, comprising the steps of:

a) operating the pace maker in a first mode for a pre-defined time period, b) generating electrical pacing pulses by means of a pulse generator of the pacemaker in the first mode and delivering the electrical pacing pulses to a pacing electrode of the pacemaker unless a sensing unit of the pacemaker senses an event corresponding to a ventricular contraction of a heart of a patient (this is also known as WI mode), c) sensing a signal related to the patient in the first mode and determining from the signal for each applied electrical pacing pulse or sensed event a value of a parameter that depends on the atrioventricular (AV) delay of the heart, wherein the respective value is stored in a memory of the pacemaker, d) generating a reference curve in the first mode, wherein the reference curve associates each determined value of the parameter with an atrioventricular delay value, e) selecting a target range of values of the parameter in the first mode, wherein the target range corresponds to a desired range of atrioventricular delays, f) operating the pacemaker in a second mode following the first mode, g) determining a value of the parameter for every heartbeat of the patient in the second mode, and h) wherein when the respective value of the parameter determined in the second mode for a heartbeat is outside the target range, the timing of an electrical pacing pulse for the next heartbeat is adjusted such that a determined value of the parameter for a succeeding heartbeat lies within or approaches the target range.

According to an embodiment of the method, the signal is indicative to one of (see also above): a pressure, a heart sound, particularly the S1 heart sound, a cardiac-wall motion (wherein particularly the sensor is an accelerometer), and a ventricular impedance (wherein particularly the sensor comprises electrodes for measuring said impedance).

Furthermore, in an embodiment of the method, for generating the reference curve, the values of the parameter determined in the first mode are sorted according to an assumed curve type, wherein particularly the curve type is monotonically decreasing. Alternatively, depending on the specific parameter, the curve type can also be monotonically increasing, bell-shaped, or parabolic.

According to a further embodiment of the method, the parameter is the amplitude of the S1 heart sound of the patient, wherein particularly the curve type is monotonically decreasing. Furthermore, in an embodiment of the method, the target range lies between the largest and the smallest determined value of the parameter (e.g. amplitude of the S1 heart sound).

Furthermore, according to an embodiment of the method, in case the respective value of the parameter (e.g. amplitude of the S1 heart sound) is below the target range, the timing of the next electrical pacing pulse is adjusted to an earlier timing so as to generate a value of the parameter for a succeeding heartbeat within or approaching the target range in order to provide AV synchrony, and wherein when the respective value of the parameter is above the target range, the pacemaker is configured to adjust the timing of the next electrical pacing pulse to a later timing so as to generate a value of the parameter for a succeeding heartbeat within or approaching the target range in order to provide AV synchrony.

Further, according to an alternative embodiment of the method, the curve type is bell-shaped, wherein particularly the target range comprises the largest determined value of the parameter (i.e. near the peak of the reference curve).

According to an embodiment of the method (e.g. in case of the bell-shaped reference curve) when the respective value of the parameter is below the target range, the timing of the next electrical pacing pulse is adjusted to an earlier timing. In case the value of the parameter increases on the next heartbeat, the timing of the electrical pacing pulse for each heartbeat is shortened until the value of the parameter reaches the target range, and in case the value of the parameter decreases, the timing of the electrical pacing pulse for each heartbeat is lengthened until the value of the parameter reaches the target range.

The features disclosed in regard with the pacemaker can be also applied to the method and vice versa.

Other features which are considered as characteristic for the invention are set forth in the appended claims.

Although the invention is illustrated and described herein as embodied in an AV synchrony with a ventricular leadless pacemaker using varying ventricular measures, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 4 is a schematical illustration of an intracardiac pacing device.

DETAILED DESCRIPTION OF THE INVENTION

Figure 1:
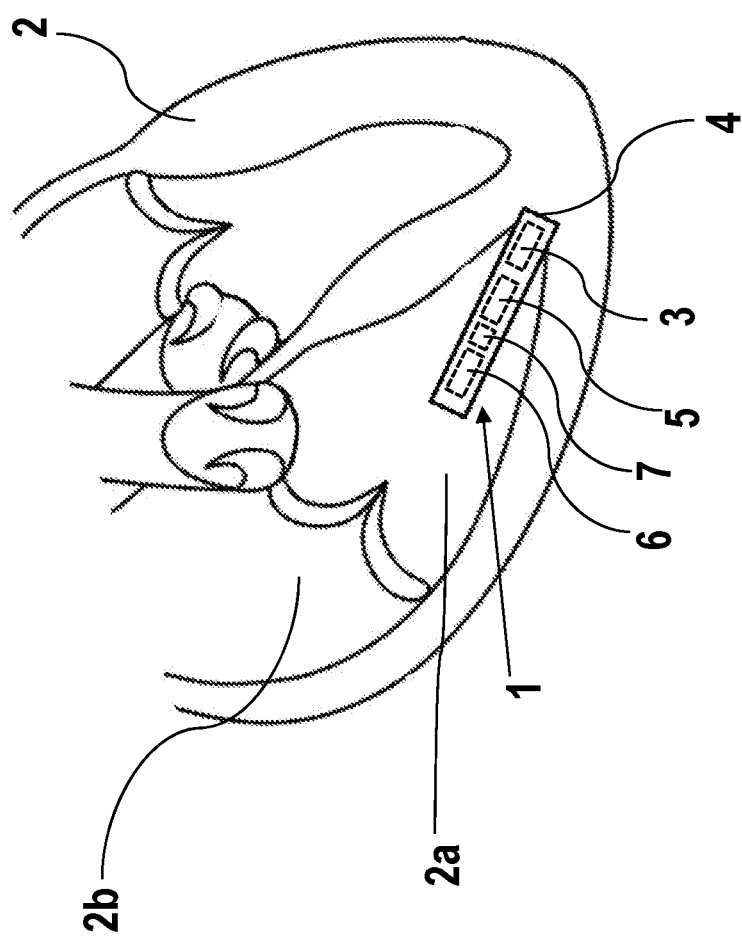
FIG. 1 is a schematical illustration of an embodiment of a pacemaker in form of an implantable leadless pacemaker that is implanted into a ventricle of the heart of the patient according to the invention.

Particularly, it is an objective to obtain beat-to-beat estimations of AV synchrony using measures of ventricular contraction of a ventricle 2a of the heart 2 of a patient, which are large and easy to detect when compared with measures of atrial contraction of an atrium 2b of the heart 2 (cf. FIG. 1).

FIG. 1 shows an embodiment of an implantable pacemaker 1, which, as shown in FIG. 1, can be an implantable leadless pacemaker 1 that is implanted in the right ventricle 2a. Particularly, the pacemaker 1 comprises a sensing unit 5 for sensing events of electrical activity of the right ventricle 2a which are indicative of a contraction of the ventricle 2a. Further, for generating electrical pacing pulses the pacemaker 1 comprises a pulse generator 3, wherein the pacing pulses are applied to the ventricle 2a via at least one pacing electrode 4.

In an embodiment, the pacemaker 1 is allowed to operate in a first mode corresponding to the VVI mode for a certain time period (e.g. hour, several hours, days, etc.). Particularly, this time period is a learning phase in which the pacemaker 1 will measure and store values of at least one parameter P associated with ventricular contraction that is known to vary with AV delay. The values can be stored in a memory 7 of the pacemaker 1. The specific ventricular contraction parameter P may be derived from a number of source signals that are measured with a sensor 6 of the pacemaker 1. Possible signals can be pressure (via a pressure sensor), heart sounds (via a microphone or accelerometer), cardiac-wall motion (via an accelerometer), or ventricular impedance (via electrodes). Each specific parameter may have unique filtering and sensing methods.

As a specific example of a possible ventricular contraction parameter P, the S1 heart sound is a result of ventricular contraction pushing blood against the closing tricuspid/mitral valves; literature shows that the amplitude of S1 monotonically decreases with longer AV delays.

Figure 2:
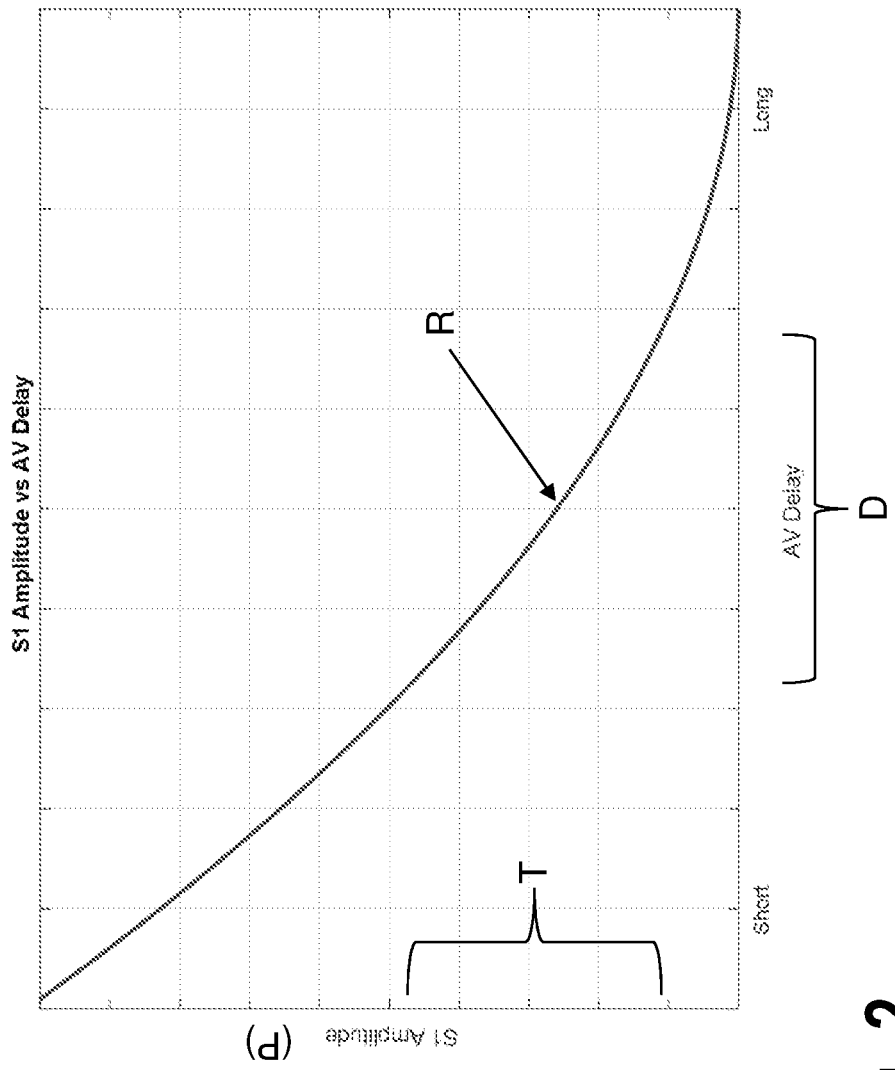
FIG. 2 is a graph showing a reference curve corresponding to an amplitude of a S1 heart sound over an AV delay.

Continuing with the specific S1 example, the pacemaker 1 operating in the first mode (e.g. VVI mode) stores the S1 amplitude for each ventricular contraction during the learning phase. Because the pacemaker is preferably in the VVI mode now, the values of the S1 amplitude stored are a mix of those resulting from intrinsic synchronized contractions, and paced asynchronous contractions; as a result, the values of the parameter P (i.e. S1 amplitude) stored correspond to a range of AV delays. Although the actual AV delay for each amplitude was not measured, because S1 is known to monotonically decrease with longer AV delays the amplitudes can be sorted by the pacemaker 1 to generate a reference curve R as shown in FIG. 2. The smallest S1 amplitudes on this curve R correspond to AV delays which were too long, while the largest S1 amplitudes on this curve R correspond to AV delays which were too short.

Once the reference curve R is generated, the pacemaker 1 selects a target range T of S1 amplitudes somewhere between the largest and shortest measured (cf. e.g. FIG. 2), which corresponds to an optimal/near-optimal range D of AV delays. This target range T of S1 amplitudes is then used in the next phase, i.e. during a second mode of the pacemaker 1.

In this next phase/second mode, the pacemaker is particularly operated in an AV synchrony mode, in which a value of the S1 amplitude is measured every heartbeat. If the value of the S1 amplitude measured is too small (right end of the reference curve R), the pacemaker 1 knows that it paced too late relative to the atrial contraction of right atrium 2b, and would therefore adjust to a shorter timing for the next heartbeat. If the value of the S1 amplitude measured is too large (left end of the reference curve R), the pacemaker 1 would know that it paced too early, and would therefore adjust to a longer timing for the next heartbeat. The pacemaker 1 therefore adjusts its pacing timing every heartbeat to aim at producing values of the S1 amplitude within the target range T of the reference-curve, which corresponds to better-synchronized AV delays.

Figure 3:
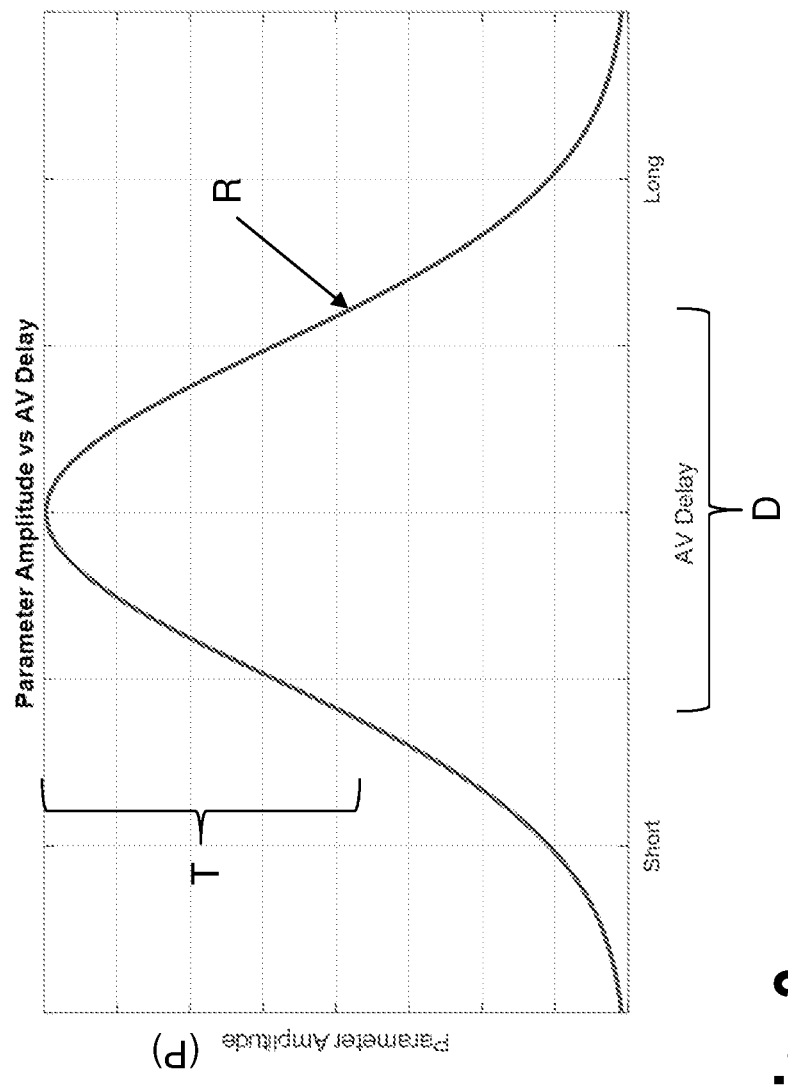
FIG. 3 is a graph of a reference curve corresponding to an amplitude of a parameter that comprises a bell-shaped curve type regarding AV delay.

The exact beat-to-beat timing adjustment depends on the exact parameter P measured and the expected curve-type for that parameter P. The embodiment described above specifically uses the amplitude of the S1 heart sound as a parameter P, but any other parameter P associated with ventricular contraction that has a relationship to AV delay can be used. For example, in another embodiment, the ventricular parameter (e.g. heart sounds, pressure, impedance, or motion) may have a bell-shaped relationship to AV delay, as shown in FIG. 3.

In this embodiment, the smallest amplitudes of a parameter P on the reference curve R correspond to AV delays which were either too short or too long. Therefore, in this embodiment (where the pacemaker 1 assumes a bell-shaped reference curve R for the parameter of interest) the pacemaker 1 selects a range of amplitudes close to the largest measured (i.e. near the peak of the reference curve R), which correspond to an optimal/near-optimal range D of AV delays for this parameter P. This range of amplitudes then becomes the target range T when the pacemaker switches to AV synchrony mode, i.e., is operated in the second mode.

In the second mode, the value of the parameter P (denoted as parameter amplitude in FIG. 3) is measured every heartbeat. If the value measured is too small, the pacemaker 1 would only know that it paced either too early or too late relative to the atrial contraction. This is due to the bell-shaped relationship to AV delay, which is not as straightforward as the monotonic relationship described above. However, the pacemaker or method can easily account for the bell-shaped case. In the bell-shaped case, if the value of the parameter P measured is too small, the pacemaker 1 can first adjust to a shorter timing for the next heartbeat (i.e. reduce the AV delay for the next heartbeat). This essentially means the pacemaker 1 first assumes that it is on the right side of the bell-shaped reference curve R shown in FIG. 3. If the value of the parameter P increases on the next heartbeat, the pacemaker 1 is be able to confirm that it is on the right side of the bell-shaped reference curve R, and would continue to shorten the timing for each heartbeat until it reaches the target range T. On the other hand, if the value of the parameter P decreases after shortening timing, the pacemaker knows that it is actually on the left side of the bell-shaped reference curve R, and would therefore begin lengthening the timing for each heart beat until it reaches the target range T.

The above are two specific examples which provide descriptions of the proposed algorithm for ventricular parameters in which the device assumes a monotonically decreasing or a bell-shaped relationship to AV delay. However, it should be apparent that the algorithm can be modified to account for other relationships in addition to these, including monotonically increasing (small amplitude with short AV delay, large amplitude with long AV delay) and parabolic (large amplitude with short and long AV delays, small amplitude with target AV delays) relationships to AV delay.

In another embodiment, the algorithm could use other parameters besides amplitude for the specific signal being measured. The other metrics could include width, frequency, spread, or variation of the signal. The pacemaker 1 would have the appropriate processing components to calculate such metrics. For example, the pacemaker 1 could generate a curve of S1 frequency vs AV delay instead of S1 amplitude vs AV delay, if it were known that S1 frequency has a monotonic, bell-shaped, or parabolic relationship to AV delay.

In another embodiment, the algorithm/pacemaker 1 could use multiple ventricular parameters with different relationships to AV delays (e.g. one with a monotonically increasing relationship, and another with a parabolic relationship) at the same time to maintain an optimal range of AV delays.

In another embodiment, the algorithm/pacemaker 1 could be extended to a single-chamber pacemaker that has the necessary sensors (pressure, accelerometer, microphone, electrodes) to measure the ventricular contraction parameters in the tip of a lead attached to the pacemaker.

FIG. 4 shows a schematic illustration of an intracardiac pacing device (also called implantable leadless pacemaker). The device comprises a housing 100 which surrounds an energy storage 102 (e.g. a battery), an electronic module 103, and a communication unit 104. The housing 100 may comprise titanium or may be made of titanium.

At a distal end of the housing 100, a first electrode 106 (also called pacing/sensing electrode) is disposed. In a proximal region of the housing 100, a second electrode 101 (also called return electrode) is arranged. The second electrode 101 may be formed as a ring electrode.

The device may be fixed to cardiac tissue by a fixation element 105. The fixation element may be formed as a tine. It may comprise Nitinol or may be made of Nitinol. In one embodiment, four tines 105 made of Nitinol may be formed at the distal end of the housing 100.

The energy storage 102 may be configured to provide electrical energy to the components of the device, in particular to the electronic module 103, the communication unit 104, and the first electrode 106.

The electronic module 103 may be configured to perform the functions of a pacemaker, including sensing cardiac events and providing pacing pulses. The electronic module 103 may comprise a processor and memory and/or state machine logic.

The communication unit 104 may be configured for communication with an external device (e.g. a programmer). The communication unit 104 may comprise a coil for inductive communication.

The intracardiac pacing device according to FIG. 4 may comprise a sensing unit for sensing events of electrical activity of the right ventricle 2a and may be configured to execute the method disclosed herein for achieving AV synchrony.

The technical advantage of the present invention is that it provides AV synchrony by relying on large signal components associated with ventricular contraction as opposed to small signal components associated with atrial contraction. As a specific example, the S1 heart sound has a large amplitude and is nearly always present, whereas the S4 heart sound due to atrial contraction has a very small amplitude and is often not present. Therefore, the pacemaker 1 and method may be more reliable than solutions depending on a small atrial signal to provide AV synchrony.

Furthermore, measures of ventricular contraction occur within a short and often well-defined window after ventricular depolarization. This is in contrast with the often long and ill-defined window after ventricular depolarization in which an algorithm must search for a measure of atrial contraction. As a result, using ventricular contraction measures instead of atrial contraction measures may improve battery lifetime of the pacemaker 1 by reducing the time in which a detection algorithm must run.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. An implantable pacemaker configured to provide electrical pacing pulses to a heart of a patient, the implantable pacemaker comprising:
 a pulse generator configured to generate the electrical pacing pulses;
 at least one pacing electrode to apply the electrical pacing pulses to the heart;
 a sensing unit configured to sense events of electrical activity of a ventricle of the heart, wherein a respective event corresponds to a contraction of the ventricle,
 a sensor configured to measure a signal relating to the patient; and
 a memory configured to store values of a parameter;
 the implantable pacemaker is configured to be operated in a first mode, wherein in the first mode, the implantable pacemaker is configured to apply the electrical pacing pulses generated by said pulse generator to the ventricle via said at least one pacing electrode unless said sensing unit senses an event, and to determine from the signal for each applied electrical pacing pulse or sensed event a value of the parameter that varies with an atrioventricular delay of the heart, wherein the implantable pacemaker is configured to store the values of the parameter in said memory, and wherein the implantable pacemaker is further configured to generate in the first mode a reference curve which associates each determined value of the parameter with the atrioventricular delay value, and to select a target range of values of the parameter corresponding to a desired range of atrioventricular delays; and
 the implantable pacemaker is further configured to be operated in a second mode, wherein in the second mode, the implantable pacemaker is configured to determine a value of the parameter for every heartbeat of the patient, wherein when a respective value of the parameter determined in the second mode for a heartbeat is outside the target range, the implantable pacemaker is configured to adjust a timing of an electrical pacing pulse for a next heartbeat such that a determined value of the parameter for a succeeding heartbeat approaches the target range.

2. The implantable pacemaker according to claim 1, wherein the signal is selected from the group consisting of a pressure, a heart sound, a cardiac-wall motion, and a ventricular impedance.

3. The implantable pacemaker according to claim 1, wherein for generating the reference curve the implantable pacemaker is configured to sort the values of the parameter determined in the first mode according to an assumed curve type.

4. The implantable pacemaker according to claim 3, wherein the assumed curve type is monotonically decreasing.

5. The implantable pacemaker according to claim 1, wherein the parameter is an amplitude of a S1 heart sound of the patient.

6. The implantable pacemaker according to claim 1, wherein the target range lies between a largest and a smallest determined value of the parameter.

7. The implantable pacemaker according to claim 5, wherein when the respective value of the parameter is below the target range, the implantable pacemaker is configured to adjust a timing of a next electrical pacing pulse to an earlier timing so as to generate a value of the parameter for a succeeding heartbeat approaching the target range, and wherein when the respective value of the parameter is above the target range, the implantable pacemaker is configured to adjust the timing of the next electrical pacing pulse to a later timing so as to generate a value of the parameter for a succeeding heartbeat approaching the target range.

8. The implantable pacemaker according to claim 1, wherein the curve type is bell-shaped.

9. The implantable pacemaker according to claim 8, wherein the target range contains a largest determined value of the parameter.

10. The implantable pacemaker according to claim 8, wherein when the respective value of the parameter is below the target range, the implantable pacemaker is configured to adjust a timing of a next electrical pacing pulse to an earlier timing, wherein in case the value of the parameter increases on the next heartbeat, the implantable pacemaker is configured to continue to shorten a timing of the electrical pacing pulse for each succeeding heartbeat until the value of the parameter reaches the target range, and wherein in case the value of the parameter decreases, the implantable pacemaker is configured to lengthen the timing of the electrical pacing pulse for each succeeding heartbeat until the value of the parameter reaches the target range.

11. The implantable pacemaker according to claim 1, wherein the curve type is one of monotonically increasing or parabolic.

12. A method for operating an implantable pacemaker, which comprises the steps of:
 operating the implantable pacemaker in a first mode for a pre-defined time period;
 generating electrical pacing pulses by means of a pulse generator of the implantable pacemaker in the first mode and delivering the electrical pacing pulses to a pacing electrode of the implantable pacemaker unless a sensing unit of the implantable pacemaker senses an event corresponding to a ventricular contraction;

sensing a signal related to a patient in the first mode and determining from the signal for each applied electrical pacing pulse or sensed event a value of a parameter that varies with an atrioventricular delay of a heart, wherein the value is stored in a memory of the implantable pacemaker;

generating a reference curve in the first mode, wherein the reference curve associates each determined value of the parameter with an atrioventricular delay value;

selecting a target range of values of the parameter in the first mode, the target range corresponding to a desired range of atrioventricular delays;

operating the implantable pacemaker in a second mode following the first mode; and determining a respective value of the parameter for every heartbeat of the patient in the second mode, when the respective value of the parameter determined in the second mode for the heartbeat is outside the target range, a timing of an electrical pacing pulse for a next heartbeat is adjusted such that a determined value of the parameter for a succeeding heartbeat approaches the target range.

13. The method according to claim 12, wherein the signal corresponds to one of: a pressure, a heart sound, a cardiac-wall motion, and a ventricular impedance.

14. The method according to claim 12, wherein for generating the reference curve values of the parameter determined in the first mode are sorted according to an assumed curve type.

15. The method according to claim 12, wherein the parameter is an amplitude of a S1 heart sound.

* * * * *